United States Patent
Tognella et al.

[11] Patent Number: 5,442,102
[45] Date of Patent: Aug. 15, 1995

[54] GEM-DIPHOSPHONIC ACID NITROSOCARBAMOYL DERIVATIVES, A PROCESS FOR THE PREPARATION THEREOF AND PHARMACEUTICAL COMPOSITIONS CONTAINING THEM

[75] Inventors: Sergio Tognella; Valeria Livi; Ernesto Menta; Silvano Spinelli, all of Milan, Italy

[73] Assignee: Boehringer Mannheim Italia S.p.A., Milan, Italy

[21] Appl. No.: 129,099
[22] PCT Filed: Apr. 3, 1992
[86] PCT No.: PCT/EP92/00745
   § 371 Date: Oct. 8, 1993
   § 102(e) Date: Oct. 8, 1993
[87] PCT Pub. No.: WO92/18511
   PCT Pub. Date: Oct. 29, 1992

[30] Foreign Application Priority Data
Apr. 12, 1991 [IT] Italy .............................. MI91A1017

[51] Int. Cl.⁶ ............................ C07F 9/38; C07F 9/40; A61K 31/66
[52] U.S. Cl. ...................... 562/13; 558/155; 558/159
[58] Field of Search .................. 562/13; 514/107, 108; 558/155, 159

[56] References Cited

U.S. PATENT DOCUMENTS

| | | | |
|---|---|---|---|
| 4,567,169 | 1/1986 | Lavielle et al. | 514/89 |
| 4,608,368 | 8/1986 | Blum et al. | 514/107 |
| 4,666,895 | 5/1987 | Bosies et al. | 514/108 |
| 5,019,651 | 5/1991 | Kieczykowski | 562/13 |
| 5,300,671 | 4/1994 | Tognella et al. | 558/159 |

FOREIGN PATENT DOCUMENTS

| | | |
|---|---|---|
| 0170896 | 2/1986 | European Pat. Off. |
| 0197478 | 10/1986 | European Pat. Off. |
| 2536075 | 5/1984 | France |

*Primary Examiner*—José G. Dees
*Assistant Examiner*—Barbara S. Frazier
*Attorney, Agent, or Firm*—Nikaido, Marmelstein, Murray & Oram

[57] ABSTRACT

Diphosphonic acids of formula (I) are disclosed. These compounds are useful as antitumor agents.

8 Claims, No Drawings

GEM-DIPHOSPHONIC ACID NITROSOCARBAMOYL DERIVATIVES, A PROCESS FOR THE PREPARATION THEREOF AND PHARMACEUTICAL COMPOSITIONS CONTAINING THEM

This application is a 35 C.S.C. 371 of PCT/EP92/00745, filed Apr. 3, 1992.

The present invention relates to diphosphonic acids having a marked antitumour activity, to a process for the preparation thereof and to pharmaceutical compositions containing them.

Gem-diphosphonic acids and the salts thereof are known and used in the treatment of osteoporosis and of bone resorption (see EP 96.931, EP 197,478 EP 252.504, BE 896.453, BE 903.519, DE 3.016.289, DE 3.540.150, DE 2.534.391).

Moreover, diphosphonic acid esters having pesticide activity are disclosed in U.S. Pat. No. 3,906,062. However, no compounds described in the above mentioned patents have been reported to have intrinsic antitumour activity.

DE 3.425.812 discloses 1,1-diphosphonic acid derivatives having a bis[(haloalkyl)amino]phenyl residue as agents useful for the treatment of bone tumours. In fact, beside having the bone tropism characteristic of diphosphonic acids, they also have the typical cytotoxic activity of molecules bearing dialkylating functions.

Metotrexate diphosphonic analogs are described in WO 88/06158 to be useful agents in the treatment of bone tumours.

Moreover, nitrosoureas, in which the nitrosocarbamoyl residue is bound to an amino acid or to ester or amido derivatives thereof, are known to have favourable pharmacokinetic and therapeutical properties in the treatment of leukemias (see: Arch. Pharm., 317, 481 (1984); J.Cancer Res. Oncol., 108, 249 (1984); J. Med. Chem. 25, 829 (1982)).

FR 2,536,075 discloses (N-(2-cloroethyl-N-nitrosoureido) phosphonic acid derivatives useful in the therapy of tumors and carcinomas.

Now it has been found that diphosphonic acid derivatives bearing the residue from a chloroethylnitrosourea have a high affinity to bone tissue, wherein the cytotoxic species is mainly released, and therefore they have advantageous antitumour and antimetastatic properties, compared with the above cited compounds.

The present invention relates to compounds of formula (I)

$$\text{Cl}-\text{CH}_2\text{CH}_2-\underset{\underset{\text{NO}}{|}}{N}-\overset{O}{\underset{||}{C}}-\left[\underset{\underset{O}{||}}{\underset{|}{\overset{R_5}{N}}-\text{CH}-\overset{R_4}{\underset{|}{C}}}\right]_q-\underset{\underset{B}{|}}{\overset{R_3}{N}}-A\overset{O}{\underset{||}{\overset{}{\underset{P}{\diagup}}}}\begin{matrix}\text{OR}_1\\\text{OR}_2\end{matrix}\quad\text{I}$$

wherein:

$R_1$ and $R_2$, which are the same or different, are hydrogen or $C_1$-$C_4$ alkyl;

A is hydrogen, halogen (chlorine, bromine or iodine), hydroxy, straight or branched $C_1$-$C_{12}$ alkyl;

B is a covalent bond, a straight or branched $C_1$-$C_8$ alkylene chain, an alkylene chain containing at least one hetero-atom of formula $-[\text{CH}(\text{CH}_3)]_p-(\text{CH}_2)_{n1}-X-(\text{CH}_2)_n-$ or, B forms:

a) Cycloaliphatic rings of formulae b) heterocyclic rings of formulae if $R_3$ is absent and together with the adjacent nitrogen atom c) an ortho, meta or para substituted aralkyl of formula X is O, S, N—CH$_3$;

m is zero or the integer 1 or 2;

$m_1$ is the integer 1, 2, 3 or 4;

n and $n_1$ are an integer from 1 to 5; p is zero or the integer 1; $R_3$ is hydrogen, straight or branched $C_1$-$C_9$ alkyl, $C_3$-$C_6$ cycloalkyl, benzyl, phenyl, or p-methoxybenzyl;

$R_4$ and $R_5$, together with the $$-\underset{|}{N}-\underset{|}{\text{CH}}-\text{CO}-$$

group to which they are linked, are the residue from a D or L amino acid; q is zero or 1.

The present invention also relates to racemates, diastereoisomers and optically pure forms of compounds of general formula (I).

The present invention also relates to the pharmaceutically acceptable salts of compounds of general formula (I), for example with inorganic bases, such as salts with alkali metals (such as sodium or potassium) or alkaline-earth metals (such as calcium or magnesium) or ammonium salts; salts with organic bases such as methylamine, ethylamine, propylamine, isopropylamine, butylamine, t-butylamine, dimethylamine, diethylamine, diethanolamine, trimethylamine, triethylamine, piperidine, pyridine, picoline, dicyclohexylamine; organic acid addition salts, such as: formate, acetate, trifluoroacetate, maleate, fumarate, tartrate, methanesulfonate, benzenesulfonate, toluenesulfonate salts; inorganic acid addition salts, such as hydrochloride, hydrobromide, sulfate, hydrogen sulfate, phosphate salts; or with amino acids, such as aspartate, glutamate, lysine or arginine salts.

$C_1$-$C_4$ Alkyl includes methyl, ethyl, n-propyl, isopropyl, n-butyl, t-butyl, isobutyl or sec-butyl; methyl and ethyl being particularly preferred.

$C_1$-$C_{12}$ Alkyl group besides the meanings precised above for $C_1$-$C_4$ alkyl, can be n-pentyl, n-hexyl, n-decyl and the like; methyl and ethyl being particularly preferred.

A is preferably hydroxy.

The alkylene chain B is preferably —(CH$_2$)$_n$—, with n comprised from 2 to 5, $$-CH-(CH_2)_r-$$
$$|$$
$$CH_3$$

with r comprised from 2 to 5, or one of the chains of formulae with n comprised from 1 to 4;

or, considered together with the adjacent nitrogen atom, one of the chains of formulae with n comprised from 1 to 3.

R$_1$ and R$_2$ are preferably hydrogen.

R$_3$ is preferably hydrogen or methyl;

R$_4$ and R$_5$, taken together with the $$|\quad|$$
$$-N-CH-CO-$$

group to which they are linked, are preferably the residue from the D or L amino acids glycine, sarcosine, alanine, phenylalanine, valine, leucine, isoleucine, methionine, proline.

Examples of compounds of the invention are:

N-[N'-(2-chloroethyl)-N'-nitrosocarbamoyl]-2-amino-1-hydroxyethane-1,1-diphosphonic acid N-[N'-(2-chloroethyl)-N'-nitrosocarbamoyl]-3-amino-1-hydroxypropane-1,1-diphosphonic acid N-[N'-(2-chloroethyl)-N'-nitrosocarbamoyl]-4-amino-1-hydroxybutane-1,1-diphosphonic acid N-[N'-(2-chloroethyl)-N'-nitrosocarbamoyl]-5-amino-1-hydroxypentane-1,1-diphosphonic acid N-[N'-(2-chloroethyl)-N'-nitrosocarbamoyl]-6-amino-1-hydroxyhexane-1,1-diphosphonic acid N-[N'-(2-chloroethyl)-N'-nitrosocarbamoyl]-4-amino-1-hydroxypentane-1,1-diphosphonic acid N-[N'-(2-chloroethyl)-N'-nitrosocarbamoyl]-3-(2-aminociclopen-1-yl)-1-hydroxypropane-1,1-diphosphonic acid N-methyl-N-[N'-(2-chloroethyl)-N'-nitrosocarbamoyl]-5-amino-1-hydroxypentane-1,1-diphosphonic acid N-[N'-(2-chloroethyl)-N'-nitrosocarbamoyl]-4-amino-4,4-pentamethylene-1-hydroxybutane-1,1-diphosphonic acid N-[N'-(2-chloroethyl)-N'-nitrosocarbamoyl]-4-amino-4,4-tetramethylene-1-hydroxybutane-1,1-diphosphonic acid 3-[4-[N'-(2-chloroethyl)-N'-nitrosocarbamoyl)-piperazin-1-yl]-1-hydroxypropane-1,1-diphosphonic acid 4-[4-[N'-(2-chloroethyl)-N'-nitrosocarbamoyl)-piperazin-1-yl]-1-hydroxybutane-1,1-diphosphonic acid N-[N'-(2-chloroethyl)-N'-nitrosocarbamoyl]-3-(pyrrolidin-2-yl)-1-hydroxypropane-1,1-diphosphonic acid N-[N'-(2-chloroethyl)-N'-nitrosocarbamoyl]-3-(piperidin-4-yl)-1-hydroxypropane-1,1-diphosphonic acid N-[N'-(2-chloroethyl)-N'-nitrosocarbamoyl]-3-(piperidin-2-yl)-1-hydroxypropane-1,1-diphosphonic acid N-[N'-(2-chloroethyl)-N'-nitrosocarbamoyl]-2-(piperidin-2-yl)-1-hydroxyethane-1,1-diphosphonic acid N-[[N'-(2-chloroethyl)-N'-nitrosocarbamoyl]-(L)-alanyl]-4-amino-1-hydroxybutane-1,1-diphosphonic acid N-[[N'-(2-chloroethyl)-N'-nitrosocarbamoyl]-(D)-alanyl]-4-amino-1-hydroxybutane-1,1-diphosphonic acid N-[[N'-(2-chloroethyl)-N'-nitrosocarbamoyl]-(L)-alanyl]-5-amino-1-hydroxypentane-1,1-diphosphonic acid N-[[N'-(2-chloroethyl)-N'-nitrosocarbamoyl]glycyl]-4-amino-1-hydroxybutane-1,1-diphosphonic acid N-[[N'-(2-chloroethyl)-N'-nitrosocarbamoyl]glycyl]-5-amino-1-hydroxypentane-1,1-diphosphonic acid N-methyl-N-[[N'-(2-chloroethyl)-N'-nitrosocarbamoyl]glycyl]-4-amino-1-hydroxybutane-1,1-diphosphonic acid N-[[N'-(2-chloroethyl)-N'-nitrosocarbamoyl]-(L)-prolyl]-3-amino-1-hydroxypropane-1,1-diphosphonic acid 3-[4-[[N'-(2-chloroethyl)-N'-nitrosocarbamoyl]-(L)-alanyl]-pyperazin-1-yl]-1-hydroxypropane-1,1-diphosphonic acid N-[[N'-(2-chloroethyl)-N'-nitrosocarbamoyl]-(D)-leucyl]-3-amino-1-hydroxypropane-1,1-diphosphonic acid N-[[N'-(2-chloroethyl)-N'-nitrosocarbamoyl]sarcosyl]-4-amino-1-hydroxybutane-1,1-diphosphonic acid N-[[N'-(2-chloroethyl)-N'-nitrosocarbamoyl]-(D)-valyl]-5-amino-1-hydroxypentane-1,1-diphosphonic acid N-[[N'-(2-chloroethyl)-N'-nitrosocarbamoyl]-(L)-γ-glutamyl]-5-amino-1-hydroxypentane-1,1-diphosphonic acid N-[[N'-(2-chloroethyl)-N'-nitrosocarbamoyl]-(L)-γ-glutamyl]-4-amino-1-hydroxybutane-1,1-diphosphonic acid.

The compounds of the present invention are prepared by reacting a compound of formula (II)

wherein T is a carboxy-activating group, with a compound of formula (III)

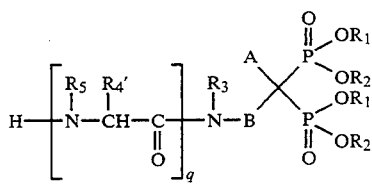

wherein $R_1$, $R_2$, $R_3$, $R_5$, A, B, q have the above mentioned meanings and $R'_4$ is the same as $R_4$ or it can be converted into $R_4$ by removal of any protecting groups present, to give a compound of formula (Ia)

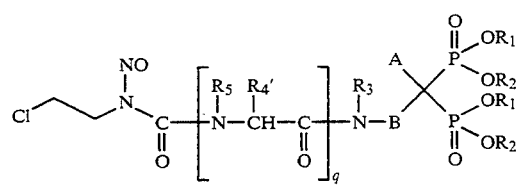

wherein $R_1$, $R_2$, $R_3$, $R'_4$, $R_5$, B, A and q have the above mentioned meanings, which compound in its turn can be transformed into a compound of formula (I) by means of known reactions for the selective removal of protecting groups.

Examples of carboxy-activating groups are azide; reactive esters (such as 1,2,2,2-tetrachloroethyl ester, ortho- or para-nitrophenyl ester, ortho- or para-cyanophenyl ester, methoxymethyl ester, 2,4-dinitrophenyl ester, pentachlorophenyl ester, hydroxysuccinimide ester, 1-hydroxy-2-(1H)-pyridone ester, 1-hydroxybenzotriazole ester, and the like). The reaction can be performed in the presence of an inorganic base, such as an alkali carbonate or bicarbonate, an alkali or alkaline-earth hydroxide or an organic base such as triethylamine, tributylamine, pyridine, 4-dimethylamino-pyridine, N-alkylmorpholine, N,N-dialkylaniline and the like.

The reaction can be effected at a temperature ranging from −40° C. to the reflux temperature of the solvent preferably using a slight molar excess of compound (II) to compound (III) in a solvent such as water, pyridine or N,N-dimethylformamide or mixtures thereof.

The reaction temperature preferably ranges from −10° C. to room temperature and, in this case, the reaction time ranges from a few minutes to some hours, but generally the reaction is complete within a time from 1 to 2 hours.

Compounds of general formula (II) are known compounds, which can be prepared by known methods, such as those described in J. Med. Chem. 25, 178,(1982), EP 290,313, Synth.,1027, (1987), J. Med. Chem., 22,200 (1979), Arch. Pharm., 317, 481,(1984).

Compounds of general formula (III) are also known and/or they can be prepared according to known methods; see, for instance, EP 96.931, EP 252.504, BE 903.519 DE 3.016.289, EP 224.751, DE 2.534.391, EP 197.478, DE 3.512.536, DE 3.623,397.

The compounds of the invention have high cytotoxic activity against tumour cells, as it can be evidenced by "in vitro" tests effected, for example, according to the procedure described by M. P. Hacker, Cancer Res. 45, 4748, (1985). The $ID_{50}$, i.e. the compound concentrations inhibiting by 50% the "in vitro" growth of murine and human tumour cells of both solid and liquid tumours, were found to be comprised from 0.1 to 5 δ/ml.

Under these test conditions, the compounds of the invention: N-[N'-(2-chloroethyl)-N'-nitrosocarbamoyl]-5-amino-1-hydroxypentane-1,1-diphosphonic acid trisodium salt and N-[N'-(2-chloroethyl)-N'-nitrosocarbamoyl]-4-amino-1-hydroxybutane-1,1-diphosphonic acid trisodium salt have an $ID_{50}$ cf 0.1 δ/ml and 0.5 δ/ml, respectively, against murine leukemia L1210.

The compounds of the invention are characterized by a low acute toxicity and are well tolerated by the animal.

The compounds of the invention have a high therapeutic index, in light of the low toxicity as well as of the effective antitumour activity thereof. Moreover, the high water-solubility of the present compounds allows the easy preparation of parenteral and oral pharmaceutical forms.

The compounds of formula (I), when administered to humans and animals affected with tumours which can be treated with alkylating agents, at doses ranging from 1 mg to 1200 mg/m² body area, can induce the regression of said tumours. The effective dosage for the compounds of the invention can be determined by the expert clinician, according to conventional methods.

The relationship between dosages used for various animal species and those for human (on the basis of mg/m² body area) is described by Freireich,.J., et al., Cancer Chemother. Rep., 50, n.4, 219–244, May 1966.

Tumours which can be treated with the compounds of the present invention are those susceptible to therapy with alkylating agents. Particularly, multiple myeloma, osteosarcoma, bone metastasis, and breast, ovarian and testis carcinomas can be advantageously treated.

Moreover, the compounds of the invention can advantageously be used in the therapy of other solid and liquid tumours, such as lymphomas and leukemias.

The compounds of the invention can be administered by the parenteral route (intravenously, intramuscularly, intraarterially, intraperitoneally) in form of sterile aqueous solutions or sterile powders for the extemporary preparation of solutions, oily preparations for the intramuscular or intraperitoneal administrations.

The compounds of the invention can also be administered by the oral route: in this instance, useful pharmaceutical formulations can be syrups or similar liquid formulations, as well as solid formulations, such as tablets, capsules and the like.

The following Examples further illustrate the invention.

EXAMPLE 1

A solution of N-(2-chloroethyl)-N-nitrosocarbamic acid hydroxysuccinimide ester (225 mg) in dimethylformamide (DMF, 2 ml) is slowly dropped into a solution of 4-amino-1-hydroxybutane-1,1-diphosphonic acid (200 mg) in water (2 ml) and 1N NaOH (2.25 ml). When dropping the ester solution, more 1N NaOH is added (0.75 ml) to maintain pH ≧8. At the end of the addition, the solution is diluted with acetone (10 ml) to obtain a precipitate which is filtered under a nitrogen atmosphere and washed with methanol to give 240 mg of N-[N'-(2-chloroethyl)-N'-nitrosocarbamoyl]-4-amino-1-hydroxybutane-1,1-diphosphonic acid trisodium salt, as a pale yellow solid. M.p.>260° C.

$^1$H-NMR (TMS, $D_2O$); δ=1,8–2,1 (m, 4H); 3,45 (t, 2H), 3,6 (t, 2H); 4,18 (t, 2H).

HPLC: 5 ODS 3, 230 mm; flow - 1,3 ml/min; λ=230 nm.

eluent: tetrabutylammonium hydrogen sulfate 4 mg/ml in water/acetonitrile/dioxane 80/15/5;
Retention time: 11,76'.

EXAMPLE 2

Following the procedure described in Example 1, by reacting N-(2-chloroethyl)-N-nitrosocarbamic acid hydroxysuccinimide ester with the appropriate aminoalkyl-1-hydroxy-1,1-diphosphonic acids, the following compounds are obtained:

N-[N'-(2-chloroethyl)-N'-nitrosocarbamoyl]-5-amino-1-hydroxypentane-1,1-diphosphonic acid trisodium salt m.p.>260° C.

$^1$N-NMR (TMS, D$_2$O) δ=1,55–1,75 (m, 4H); 1,8–2,1 (m, 2H); 3,45 (t, 2H); 3,6 (t, 2H); 4,2 (t, 2H).

HPLC: 5 ODS 3, 250 mm; flow=1,3 ml/min; λ=230 nm; eluent: 4 mg/ml of tetrabutylammonium hydrogen sulfate in water acetonitrile/dioxane 80/15/5.

Retention time: 14,01';

N-[N'-(2-chloroethyl)-N'-nitrosocarbamoyl]-3-amino-1-hydroxypropane-1,1-diphosphonic acid (trisodium salt);

N-[N'-(2-chloroethyl)-N'-nitrosocarbamoyl]-6-amino-1-hydroxyhexane-1,1-diphosphonic acid (trisodium salt);

N-[N'-(2-chloroethyl)-N'-nitrosocarbamoyl]-4-amino-1-hydroxypentane-1,1-diphosphonic acid (trisodium salt);

N-[N'-(2-chloroethyl)-N'-nitrosocarbamoyl]-3-(2-aminociclopent-1-yl)-1-hydroxypropane-1,1-diphosphonic acid (trisodium salt);

N-[N'-(2-chloroethyl)-N'-nitrosocarbamoyl]-4-amino-4,4-pentamethylene-1-hydroxybutane-1,1-diphosphonic acid (trisodium salt);

N-methyl-N-[N'-(2-chloroethyl)-N'-nitrosocarbamoyl]-5-amino-1-hydroxypentane-1,1-diphosphonic acid (trisodium salt);

N-[N'-(2-chloroethyl)-N'-nitrosocarbamoyl]-4-amino-4,4-tetramethylene-1-hydroxybutane-1,1-diphosphonic acid (trisodium salt);

3-{4-[N'-(2-chloroethyl)-N'-nitrosocarbamoyl]-piperazin-1-yl}-1-hydroxypropane-1,1-diphosphonic acid (trisodium salt);

4-{4-[N'-(2-chloroethyl)-N'-nitrosocarbamoyl]-piperazin-1-yl}-1-hydroxybutane-1,1-diphosphonic acid (trisodium salt);

N-[N'-(2-chloroethyl)-N'-nitrosocarbamoyl]-3-(pyrrolidin-2-yl)-1-hydroxypropane-1,1diphosphonic acid (trisodium salt);

N-[N'-(2-chloroethyl)-N'-nitrosocarbamoyl]-3-(piperidin-4-yl)-1-hydroxypropane-1,1-diphosphonic acid (trisodium salt);

N-[N'-(2-chloroethyl)-N'-nitrosocarbamoyl]-3-(piperidin-2-yl)-1-hydroxypropane-1,1-diphosphonic acid (trisodium salt);

N-[N'-(2-chloroethyl)-N'-nitrosocarbamoyl]-2-(piperidin-2-yl)-1-hydroxyethane-1,1-diphosphonic acid (trisodium salt).

EXAMPLE 3

A solution of N-(2-chloroethyl)-N-nitrosocarbamic acid hydroxysuccinimide ester (60 mg) in DMF (1 ml) is slowly dropped into a solution of N-[(L)-alanyl]-4-amino-1-hydroxybutane-1,1-diphosphonic acid (65 mg) in water (1 ml) and 1N NaOH (0.6 ml). When dropping the ester solution, more 1N NaOH is added (0.2 ml) to maintain pH ≧8. At the end of the addition, the solution is diluted with acetone (10 ml) to obtain a precipitate which is filtered under a nitrogen atmosphere and washed with methanol to give 80 mg of N-[[N'-(2-chloroethyl)-N'-nitrosocarbamoyl]-(L)-alanyl]-4-amino-1-hydroxybutane-1,1-diphosphonic acid trisodium salt; m. p.>260° C.

$^1$H-NMR (D$_2$O, TMS): δ=1,52 (d, 3H); 1,6–2,1 (m, 4H); 3,25 (t, 2H); 3,6 (t, 2H); 4,18 (t, 2H); 4,5 (q, 1H).

EXAMPLE 4

Following the procedure described in Example 3, by reacting N-(2-chloroethyl)-N-nitrosocarbamic acid hydroxysuccinimide ester with the appropriate N-(aminoacyl)aminoalkyl-1-hydroxy-1,1-diphosphonic acids, the following compounds are obtained:

N-[[N'-(2-chloroethyl)-N'-nitrosocarbamoyl]-(D)-alanyl]-4-amino-1-hydroxybutane-1,1-diphosphonic acid (trisodium salt);

N-[[N'-(2-chloroethyl)-N'-nitrosocarbamoyl]-(L)-alanyl]-5-amino-1-hydroxypentane-1,1-diphosphonic acid (trisodium salt);

N-[[N'-(2-chloroethyl)-N'-nitrosocarbamoyl]-(D)-alanyl]-5-amino-1-hydroxypentane-1,1-diphosphonic acid (trisodium salt);

N-[[N'-(2-chloroethyl)-N'-nitrosocarbamoyl]glycyl]-4-amino-1-hydroxybutane-1,1-diphosphonic acid (trisodium salt);

N-[[N'-(2-chloroethyl)-N'-nitrosocarbamoyl]glycyl]-5-amino-1-hydroxypentane-1,1-diphosphonic acid (trisodium salt);

N-methyl-N-[[N'-(2-chloroethyl)-N'-nitrosocarbamoyl]-glycyl]-4-amino-1-hydroxybutane-1,1-diphosphonic acid (trisodium salt);

N-[[N'-(2-chloroethyl)-N'-nitrosocarbamoyl]-(L)-prolyl]-3-amino-1-hydroxypropane-1,1-diphosphonic acid (trisodium salt);

N-[[N'-(2-chloroethyl)-N'-nitrosocarbamoyl]-(L)-prolyl]-5-amino-1-hydroxypentane-1,1-diphosphonic acid (trisodium salt);

3-{4-[[N'-(2-chloroethyl)-N'-nitrosocarbamoyl]-(L)-alanyl]-piperazin-1-yl}-1-hydroxypropane-1,1-diphosphonic acid (trisodium salt);

4-{4-[[N'-(2-chloroethyl)-N'-nitrosocarbamoyl]-(L)-alanyl]-piperazin-1-yl}-1-hydroxybutane-1,1-diphosphonic acid (trisodium salt).

We claim:

1. Compounds of formula (I):

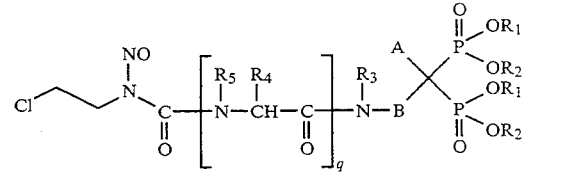

wherein:

R$_1$ and R$_2$, which are the same or different, are hydrogen or C$_1$–C$_4$ alkyl;

A is hydrogen, halogen (chlorine, bromine or iodine), hydroxy, straight or branched C$_1$–C$_{12}$ alkyl;

B is a covalent bond, a straight or branched C$_1$–C$_8$ alkylene chain, an alkylene chain containing at least one hetero-atom of formula —[CH(CH$_3$)-]$_p$—(CH$_2$)$_{ni}$—X—(CH$_2$)$_n$— or, B forms:

a) Cycloaliphatic rings of formulae

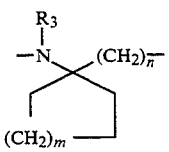 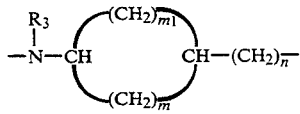

b) an ortho, meta or para substituted aralkyl of formula

X is O, S, N—CH$_3$;

m is zero or the integer 1 or 2;

m$_1$ is the integer 1, 2, 3 or 4;

n and n$_1$ are an integer from 1 to 5; p is zero or the integer 1;

R$_3$ is hydrogen, straight or branched C$_1$–C$_9$ alkyl, C$_3$–C$_6$ cycloalkyl, benzyl, phenyl, or p-methoxybenzyl;

R$_4$ and R$_5$, together with the

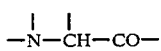

group to which they are linked, are the residue from a D or L amino acid; q is zero or 1; and isomers, diastereoisomers and pharmaceutically acceptable salts thereof.

2. Compounds according to claim 1, wherein q is zero.

3. Compounds according to claim 1, wherein q is 1 and R$_5$ and R$_4$, together with the group

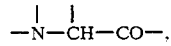

form the residue from a D or L amino acid selected from: glycine, sarcosine, alanine, phenylalanine, valine, leucine, isoleucine, methionine, proline.

4. Compounds according to claim 1, wherein A is hydroxy.

5. Compounds according to claim 1, in which B is —(CH$_2$)$_n$— wherein n is from 2 to 5, $$-\underset{\underset{CH_3}{|}}{CH}-(CH_2)_r-$$

wherein r is from 2 to 5 or one of the chains of formulae

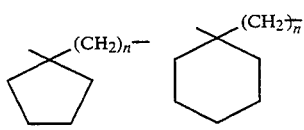

wherein n is from 1 to 4.

6. Compounds according to claim 1, wherein R$_1$ and R$_2$ are hydrogen.

7. Pharmaceutical compositions containing as the active ingredient a compound according to claim 1, in admixture with a suitable carrier.

8. A method of treatment of a patient suffering from a bone tumor comprising administering to a patient in need of such treatment an antitumor effective amount of a compound according to claim 1.

* * * * *